(12) United States Patent
Kerwin et al.

(10) Patent No.: US 6,494,864 B1
(45) Date of Patent: Dec. 17, 2002

(54) INNER LUMEN ANTI-FREE FLOW DEVICE

(75) Inventors: Michael J. Kerwin, St. Louis, MO (US); Mitchell Babkes, Maryland Heights, MO (US); Glenn G. Fournie, Smithton, IL (US); Lee C. Burnes, Attleboro, MA (US)

(73) Assignee: Sherwood Services, AG (CH)

( * ) Notice: Subject to any disclaimer, the term of this patent is extended or adjusted under 35 U.S.C. 154(b) by 330 days.

(21) Appl. No.: 09/650,302

(22) Filed: Aug. 29, 2000

(51) Int. Cl.[7] .............................................. A61M 37/00
(52) U.S. Cl. ...................................................... 604/131
(58) Field of Search .................................. 604/131, 132, 604/133, 93.01; 137/493, 45, 854, 625.47

(56) References Cited

U.S. PATENT DOCUMENTS

| | | | |
|---|---|---|---|
| 3,311,268 A | | 3/1967 | Fields |
| 3,460,529 A | | 8/1969 | Leucci |
| 3,547,401 A | | 12/1970 | Beall et al. |
| 3,786,814 A | * | 1/1974 | Armao ........................ 604/113 |
| 4,147,184 A | * | 4/1979 | Jess ....................... 137/625.47 |
| 4,263,932 A | | 4/1981 | Laar et al. |
| 4,395,260 A | | 7/1983 | Todd et al. |
| 4,615,693 A | | 10/1986 | Paradis et al. |
| 4,850,393 A | | 7/1989 | Lashomb |
| 5,019,055 A | | 5/1991 | O'Boyle |
| 5,267,566 A | | 12/1993 | Jankavaara |
| 5,396,925 A | | 3/1995 | Poli |
| 5,413,599 A | * | 5/1995 | Imachi et al. ................ 137/854 |
| 5,499,968 A | * | 3/1996 | Milijasevic et al. ........ 604/246 |
| 5,514,110 A | * | 5/1996 | Teh .............................. 137/517 |
| 5,704,584 A | * | 1/1998 | Winterer et al. ................ 251/7 |
| 5,718,569 A | * | 2/1998 | Holst ..................... 137/624.18 |
| 5,799,700 A | * | 9/1998 | Teh et al. ....................... 138/45 |
| 5,810,323 A | * | 9/1998 | Winterer et al. ................ 251/4 |
| 5,868,715 A | | 2/1999 | Tung |
| 5,954,485 A | | 9/1999 | Johnson et al. |
| 6,056,010 A | * | 5/2000 | Wells .......................... 137/614 |
| 6,110,144 A | * | 8/2000 | Choh et al. .................. 604/500 |
| 6,224,578 B1 | * | 5/2001 | Davis et al. ................. 604/247 |
| 6,447,487 B1 | * | 9/2002 | Cane' ......................... 604/131 |

FOREIGN PATENT DOCUMENTS

| | | |
|---|---|---|
| CA | 2076512 | 8/1992 |
| DE | 4126088 | 1/1993 |

* cited by examiner

*Primary Examiner*—Teresa Walberg
*Assistant Examiner*—Daniel Robinson
(74) *Attorney, Agent, or Firm*—Greensfelder, Hemker & Gale, P.C.

(57) ABSTRACT

An anti-free flow device is disclosed for a fluid administration system having a tube assembly engageable with a pump having one end of the tube assembly connected to a source of fluid and the other end in fluid flow communication with a patient. The valve device comprises a tube portion defining a channel in-line along a portion of the tube assembly and a body disposed and securely retained inside the channel. Fluid flow is initiated through the tube assembly whenever the tube assembly is in a stretched condition, such as when the tube assembly is engaged with the pump. However, fluid free flow is prevented whenever the tube assembly is in a relaxed condition or disengaged from the pump.

27 Claims, 4 Drawing Sheets

INNER LUMEN ANTI-FREE FLOW DEVICE

BACKGROUND OF THE INVENTION

1. Field of the Invention

The present invention relates to a device for preventing fluid free flow in a fluid administration system, and more particularly to an anti-free flow valve device disposed within a lumen of a tube assembly. More specifically, the present invention relates to an anti-free flow valve device that prevents fluid free flow when the tube assembly is in a relaxed condition, while permitting fluid flow when the tube assembly is in a stretched condition.

2. Prior Art

Administering fluid, such as medication, saline and nutritional formula, to a patient is generally well-known in the art. Typically, fluid is supplied to a patient by a tube assembly of a fluid administration system which provides a fluid pathway between a fluid source and the patient. The fluid is supplied to the patient through the tube assembly by either an enteral connection which accesses a visceral organ (gastrointestinal feeding) of a patient or through a parenteral connection which accesses a non-visceral organ (intravenous feeding).

Fluid flow rate through the tube assembly may be manually controlled by a mechanical clip which is designed to progressively occlude the tube assembly and selectively impede fluid flow induced by gravity. One such mechanical clip which operates to occlude a portion of the tube assembly is a conventional roller clamp that has a hollow body with opposed openings and a pair of angled slots formed opposite of one another transverse to the openings. The clip further includes a wheel having an axle which is coupled to the body through the slots. A portion of the tube assembly is then inserted through both the openings of the roller clamp and the wheel axially advanced along the slots to pinch a portion of the tube assembly against the body which progressively occludes the tube assembly. Although the mechanical clip operates to provide a cost-efficient method for controlling fluid flow rate, the clip must be manually actuated by the user. Further, the wheel of the mechanical clip can be inadvertently bumped or jostled out of position resulting in an inappropriate flow rate.

In order to better enhance fluid flow rate control in a fluid administration system, calibrated pumps have been utilized. One such calibrated pump is a peristaltic pump connected in-line along a portion of the tube assembly between the fluid source and the patient. The peristaltic pump advances the fluid through the tube assembly by progressively occluding successive portions of the tube assembly and urging each occluded portion forward by rotating the rotor of the pump. When a peristaltic pump is utilized to control the fluid flow rate, mechanical clips are typically not employed or are disengaged to prevent the clip from interfering with the operation of the pump.

Although peristaltic pumps have substantially advanced the art, further improvements are required. For example, once the tube assembly is disengaged from the rotor of the pump fluid flow rate through the tube assembly becomes unrestrained as fluid is drawn through the tube assembly by the force of gravity. This situation is known as fluid free flow and may present an undesirable, or even life-threatening situation, if left undetected because of the risk of overfeeding or overmedicating a patient.

In order to overcome the above-noted drawbacks to fluid administration systems utilizing pumps, several devices have been suggested which operate to automatically occlude a portion of the tube assembly and prevent fluid free flow when the tube assembly becomes disengaged from the rotor of the pump while also permitting uninhibited fluid flow when the tube assembly is properly engaged to the pump. For instance, a variety of automatic occluders have been suggested to improve the art such as those disclosed in U.S. Pat. No. 4,689,043 to Bisha entitled "IV Tube Activator" which describes a clamp for use with a peristaltic pump. The clamp includes a V-shaped channel which is spring biased into a closed position where the narrow portion of the V-shaped channel is sized to substantially crimp, or occlude, a portion of the tube assembly and prevent fluid free flow therethrough. The clamp is placed in an open position by a handle which overlays the pump and depresses the springs such that the tube assembly is positioned within the wider portion of the V-shaped channel to permit unrestricted fluid flow through the tube assembly when the pump is operating. When the handle is released, the V-shaped portion will automatically slide into the closed position and prevent fluid free flow by occluding a portion of the tube assembly.

Another automatic occluder is disclosed in U.S. Pat. No. 5,704,582 to Winterer, et al. entitled "Pinched Clipped Occluder for Infusion Sets" which describes a clip that is positioned between a housing and a cover of a pump. The clip has a plunger biased by a spring against the lumen of the tube assembly so that the lumen becomes occluded by the plunger. Fluid flow through the tube assembly may only be established when the plunger is biased away from the lumen of the tube assembly which occurs when the cover is properly coupled with the housing. However, once the cover becomes disengaged from the housing, the plunger is automatically biased into the closed position by the spring to prevent fluid free flow.

Although both of the aforementioned automatic occluders have advanced the art, both devices are mechanically complex and prone to mechanical failure. In addition, the mechanical complexity of these devices also results in occluders which are expensive to manufacture. Accordingly, there is a need in the art for a valve device disposed within a lumen of a tube assembly that is capable of preventing fluid free flow when the tube assembly is disengaged from the pump, while also being mechanically uncomplicated, reliable and low cost to manufacture.

OBJECTS AND SUMMARY OF THE INVENTION

In brief summary, the present invention overcomes and substantially alleviates the deficiencies present in the art by providing a valve device for a fluid administration system which is adapted to prevent fluid free flow when the tube assembly is in a relaxed condition, while permitting fluid flow when the tube assembly is engaged to the pump.

Preferably, the pump of the fluid administration system used with the present invention includes a rotor for advancing fluid through the tube assembly and a pair of recesses formed adjacent the rotor for retaining portions of the tube assembly to the housing of the pump during operation of the system. The tube assembly is an elongated tube with a lumen formed therethrough which provides a fluid pathway having three interconnected tube segments each including respective distal and proximal ends. The distal end of the first tube segment is attached to the fluid source, while the proximal end thereof is connected to the distal end of the second tube segment by a drip chamber having an abutment surface. The proximal end of the second tube segment is interconnected to the distal end of the third tube segment by a coupling having an external flange. Finally, the proximal end of the third tube segment is connected to an enteral or parental connection on the patient.

The tube assembly is engaged to the pump by engaging the second tube segment around the rotor with the abutment surface and external flange engaged within the respective recesses of the pump. Preferably, the length of the second tube segment permits the abutment surface and the external flange of the tube assembly to be properly captured by the first and second recesses, respectively, and place the second tube segment in a stretched condition around the rotor of the pump.

Preferably, the valve device comprises a body disposed in a flexible tube portion that forms a part of the valve device and is interposed between and in communication with the second tube segment and the coupling. The preferred embodiment of the body includes a sealing member formed at the distal end thereof with a plurality of legs which extend in a tapered fashion from the plunger portion and collectively terminate at an annular flange or retention member that defines an opening at the proximal end of the body. An aperture is formed between each of the legs and communicates with the opening through an inner chamber formed between the legs of the body. The tube portion is made of a flexible elastomeric material which securely houses the body inside a channel defined by the valve tube portion having proximal and distal ends. The proximal end of the channel defines a groove and the distal end forms a valve seat or outlet. The groove is formed around the wall of the channel and is sized and shaped to securely retain the retention member of the valve body within the channel. The valve seat functions as part of a sealing arrangement which is adapted to provide a fluid tight engagement with the sealing member of the body when the valve device is placed in the closed position. When the valve device is in the closed position, the head of the sealing member is securely seated against the valve seat and prevents fluid flow therethrough.

In an alternative embodiment of the body, the legs of the body extend from the sealing member in a straight fashion rather than being tapered as disclosed in the preferred embodiment. In yet another alternative embodiment, the body includes a tapered elongated shaft which extends from the sealing member and terminates at a proximal portion having opposing dual channels formed therethrough which communicate with the either side of the elongated shaft. The proximal portions of both embodiments are also configured to retain the body within the groove formed around the valve tube portion.

In operation, the valve device of the present invention prevents fluid free flow whenever the tube assembly is disengaged from the pump while also permitting fluid flow when the tube assembly is engaged around the rotor of the pump or manually actuated by the user. The body is inserted within the channel of the tube portion during manufacturing of the valve device. To utilize the valve device of the present invention with the fluid administration set, the user first connects one end of the tube assembly with a fluid source and allows fluid to travel through the tube assembly until it reaches the point where the valve device is disposed. The user then primes the tube assembly to evacuate air from all the remaining portions of the tube assembly. Preferably, the tube assembly may be manually primed by pulling or stretching the portion of the tube assembly adjacent the tube portion which pulls the body away from the coupling and unseats the sealing member from the valve seat. This operation allows fluid to flow and forces air out the remaining portions of the tube assembly until all the air is evacuated from the tube assembly. Once fluid administration system has been primed, the proximal end of the third segment may be attached to either an enternal or parenternal connection made with the patient.

To regulate and urge fluid through the tube assembly, the tube assembly is engaged around the rotor of the pump. To properly engage the tube assembly, the abutment surface of the drip chamber is inserted within the first recess of the pump, while the second tube segment is stretched by the user around the rotor. The external flange of the tube assembly is then inserted into the second recess in order to retain the second tube segment in a stretched condition around the rotor. In the stretched condition, a tensile force is applied along the second tube segment which also stretches the tube portion and places the valve device in an open position. In the open position, the body is pulled away from the valve seat which unseats the sealing member from the valve seat and permits fluid flow through the valve device. However, if the tube assembly becomes disengaged from the pump, either intentionally or unintentionally, the tensile force applied along the second tube segment and the tube portion is released which places the valve device in the closed position. In the closed position the sealing member of the body is driven back against the valve seat in fluid tight engagement as the second tube segment and the tube portion move from the stretched condition to the relaxed condition and fluid free flow is prevented through the valve device. Because the retention member of the valve body is always retained within the groove of the tube portion, the body is placed in the open position whenever the second tube segment and the valve tube portion are in the stretched condition. Conversely, the body is always placed in the closed position whenever the second tube segment and the tube portion are returned to the relaxed condition.

Accordingly, the primary object of the present invention is to provide a valve device which prevents fluid free flow in a fluid administration system.

A further object of the present invention is to provide a valve device that prevents fluid free flow whenever the tube assembly is disengaged from the pump, while permitting fluid flow whenever the tube assembly is engaged to the pump.

Another object of the present invention is to provide a valve device which prevents fluid free flow while being mechanically simple in order to reduce the opportunity of mechanical failure.

Another further object of the present invention is to provide a valve device of the above character that forms a part of the tube assembly.

These and other objects of the present invention are realized in the preferred embodiment, described by way of example and not by way of limitation, which provides for a valve device for use in a fluid administration system to prevent fluid free flow within the tube assembly whenever the tube assembly is disengaged from the pump.

Additional objects, advantages and novel features of the invention will be set forth in the description which follows, and will become apparent to those skilled in the art upon examination of the following more detailed description and drawings in which like elements of the invention are similarly numbered throughout.

DETAILED DESCRIPTION OF THE INVENTION

Figure 1:
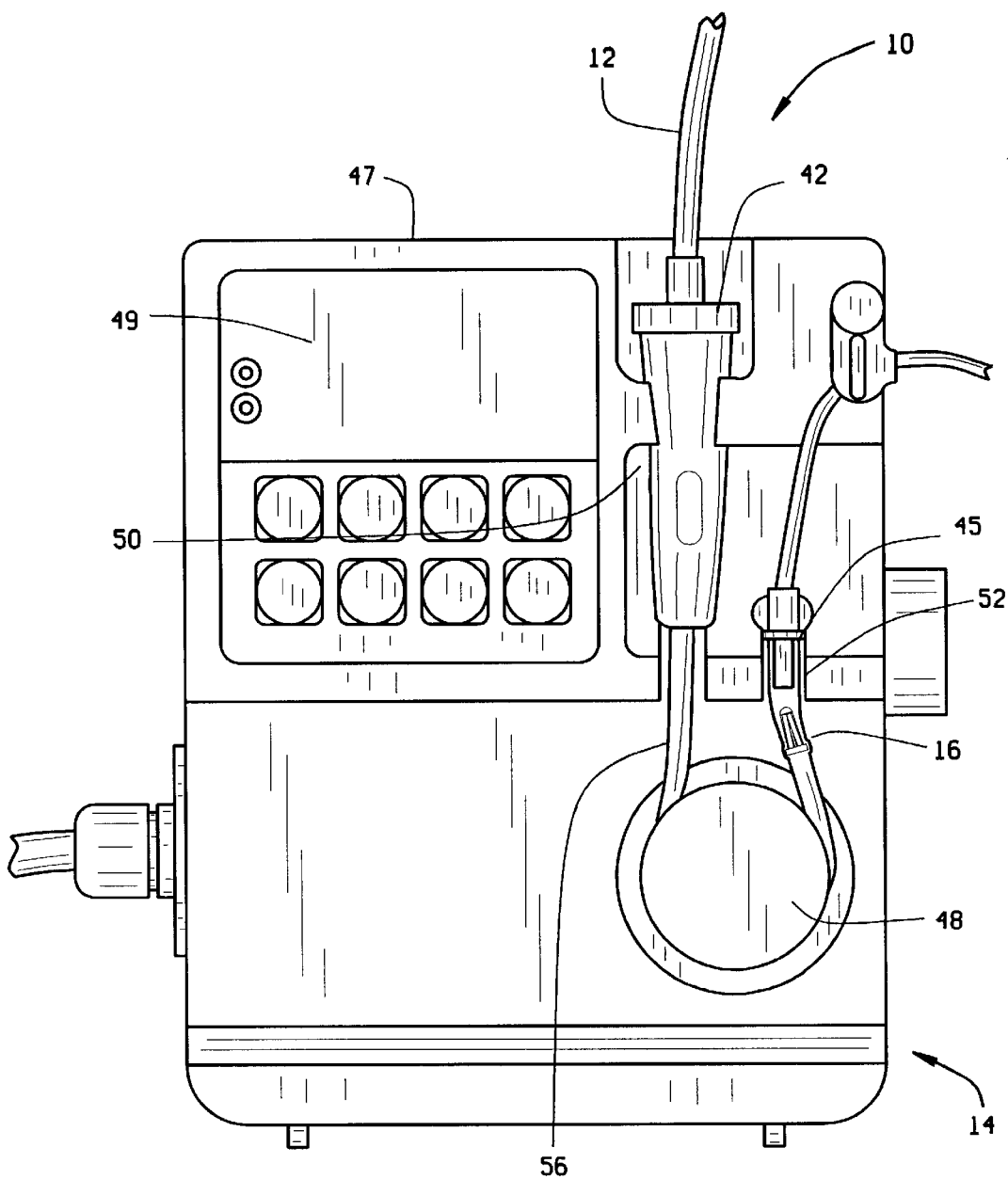
FIG. 1 is a partial front view of the tube assembly engaged with the pump according to the present invention.

Referring to the drawings, the preferred embodiment of the valve device of the present invention is illustrated and generally indicated as 16 in FIG. 1. The valve device 16 is used in a fluid administration system 10 having a tube assembly 12 and a pump 14 with device 16 disposed within tube assembly 12 for preventing fluid free flow when assembly 12 is disengaged from the pump. For ease of reference, proximal shall refer to the end of valve device 16 or tube assembly 12 closest to the fluid source 46 while distal shall refer to the end of valve device 16 or tube assembly 12 farthest from fluid source 46 as illustrated in FIG. 2.

Pump 14 is preferably a rotary peristaltic pump as shown in FIG. 1, although one skilled in the art can best appreciate that a variety of other pumps, such as linear peristaltic pumps, may be utilized with valve device 16 without departing from the novel aspects of the present invention. Specifically, pump 14 includes a housing 47 having a rotor 48 and a control panel 49 located adjacent rotor 48 which permits a user to monitor and adjust the rotation rate of rotor 48 for controlling fluid flow rate by pump 14. Housing 47 further includes a first recess 50 and a second recess 52 formed above rotor 48 for engaging and retaining a portion of tube assembly 12 in a stretched condition as will be discussed in greater detail below.

Figure 2:
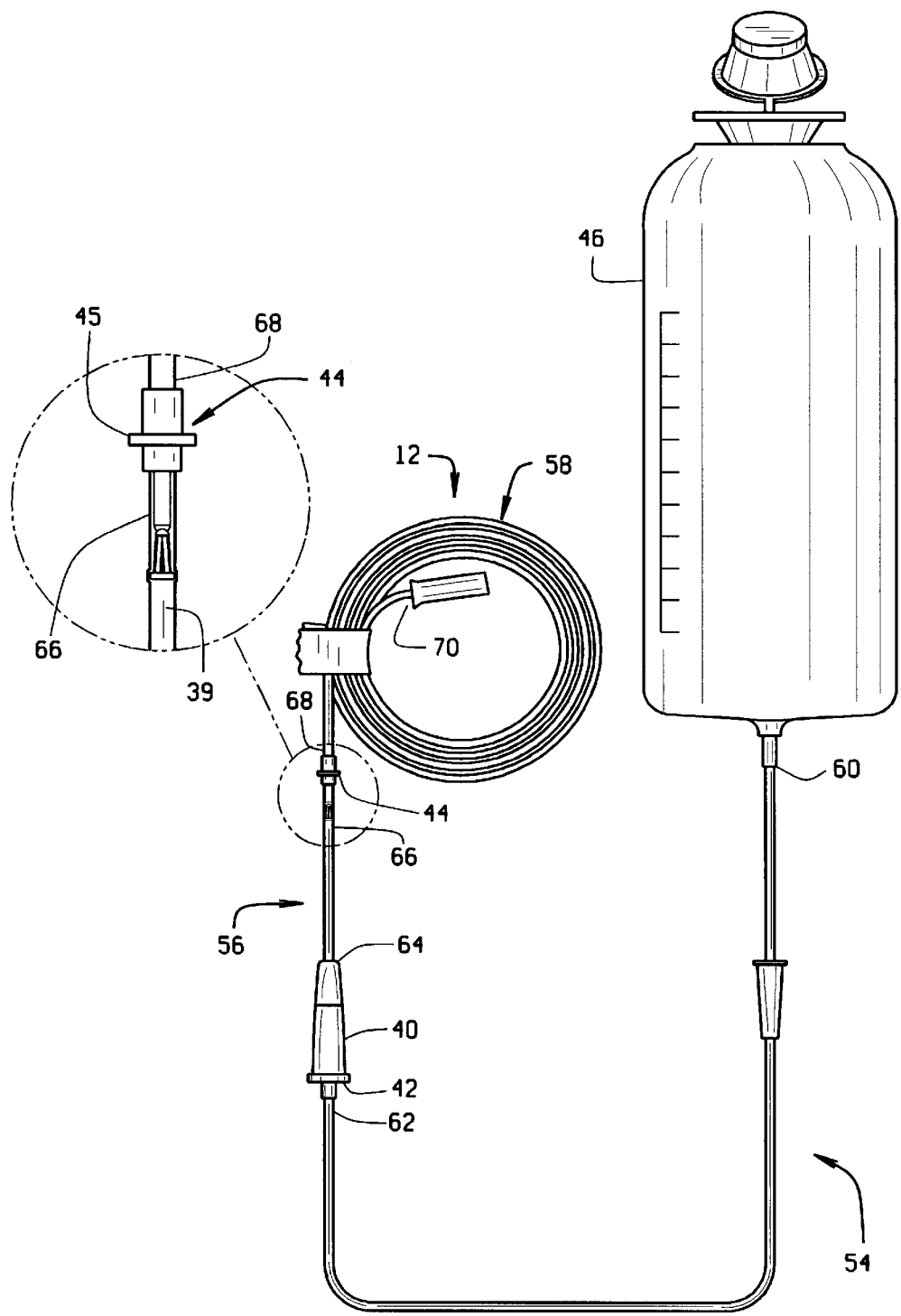
FIG. 2 is a perspective view of the fluid administration system comprising a fluid source, tube assembly and valve device according to the present invention.

Referring to FIG. 2, tube assembly 12 comprises a first tube segment 54, second tube segment 56 and third tube segment 58 which are in communication with one another through a lumen 39 with each tube segment 54, 56 and 58 having a respective proximal end 60, 64 and 68 and a respective distal end 62, 66 and 70. Proximal end 60 of first tube segment 54 is connected to fluid source 46 for providing fluid to a patient, while distal end 62 thereof is connected to an abutment surface 42 of a drip chamber 40. Drip chamber 40 is a metering system which interconnects distal end 62 with the proximal end 64 of second tube segment 56. As further shown, distal end 66 of second tube segment 56 is connected to a coupling 44 having an external flange 45 which interconnects distal end 66 with the proximal end 68 of third tube segment 56. Finally, distal end 70 of third tube segment 58 communicates with either an enternal or parenternal connection made with a patient for delivery of fluid through tube assembly 12.

As illustrated back in FIG. 1, abutment surface 42 and external flange 45 of tube assembly 12 are sized and shaped to be retained within a first recess 50 and a second recess 52, respectively, formed along the housing 47 of pump 14. The length of second tube segment 56 permits abutment surface 42 and external flange 45 to be properly captured within first recess 50 and second recess 52, respectively, while placing second tube segment 56 in a stretched condition as it is engaged around rotor 48. Accordingly, the amount of tensile force applied along second tube segment 56 as it is stretched around rotor 48 may be varied by altering the length of tube segment 56.

Figure 3:
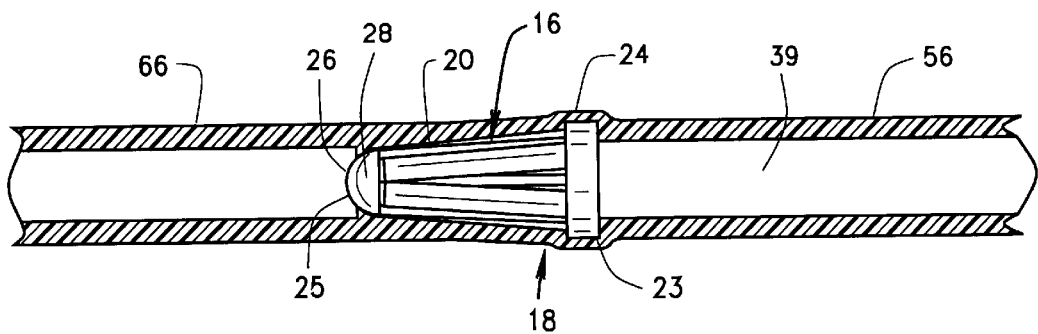
FIG. 3 is a partial cross-sectional view of the valve device shown in the closed position according to the present invention.
Figure 4:
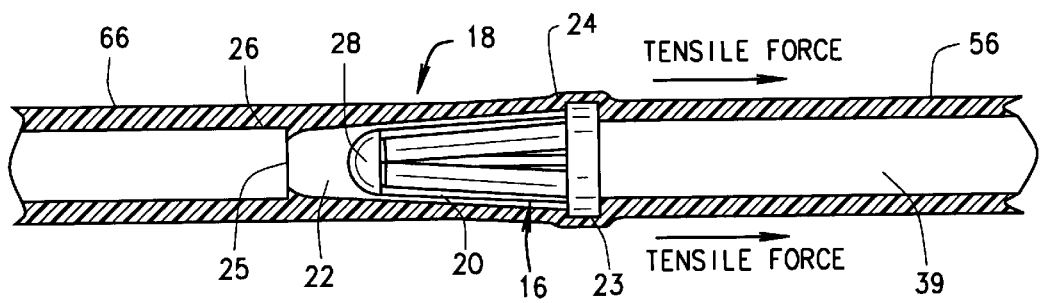
FIG. 4 is a partial cross-section view of the valve device shown in the open position according to the present invention.

Referring to FIGS. 3 and 4, the preferred embodiment of valve device 16 comprises a flexible valve tube portion 18 and solid valve body 20. Valve tube portion 18 forms a part of tube assembly 12 and is located proximate the distal end 66 of second tube segment 56 at its connection with coupling 44 (FIG. 2). A channel 22 is defined through the interior of valve tube portion 18 having a proximal section 24 and an opposing distal section 26 in communication with lumen 39. As further shown, a groove 23 is formed adjacent proximal section 24 of channel 22 and serves as a means for securely retaining valve body 20 within valve tube portion 18. The distal end 26 of channel 22 defines a valve seat 25 which forms an opening adapted to engage and seal against valve body 20 when valve device 16 is placed in the open position as shall be discussed in greater detail below. Preferably, valve tube portion 18 is constructed from an elastomeric material, such as silicone, although any suitable medical grade material that exhibits sufficient resilience and stretching characteristics when subjected to a tensile force is felt to fall within the spirit of the present invention.

Figure 5:
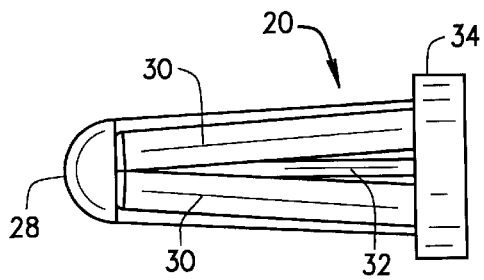
FIG. 5 is a side view of the preferred embodiment of the valve body according to the present invention.
Figure 7:
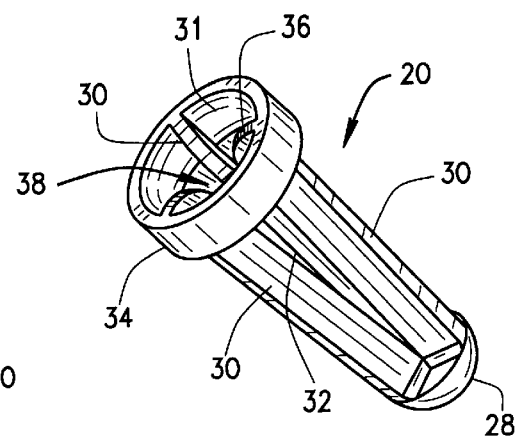
FIG. 7 is a perspective view of the preferred embodiment of the valve body according to the present invention.
Figure 6:
FIG. 6 is an end view of the preferred embodiment of the valve body according to the present invention.

Referring to FIGS. 5–7, the preferred embodiment of valve body 20 is illustrated. Valve body 20 comprises a sealing member 28 which acts as a sealing member for preventing fluid flow communication through valve device 16. Sealing member 28 has a generally dome-shaped configuration which is adapted to seat in a fluid tight engagement against valve seat 25 (FIG. 3) when valve device 16 is placed in the closed position. Valve body 20 includes a plurality of legs 30 which extend proximally from sealing member 28 in a tapered fashion and terminate along an annular-shaped retention member 34 formed at the proximal end 31 of valve body 20. Valve body 20 further includes a plurality of apertures 32 formed between each set of respective legs 30. As shown specifically in FIGS. 6 and 7, retention member 34 defines an annular-shaped opening 36 which communicates with apertures 32 through an inner chamber 38 defined between legs 30. The apertures 32, chamber 38 and opening 36 collectively provide a fluid pathway through valve body 20 when valve device 16 is placed in the open position and fluid free flow is permitted through valve tube portion 18.

In operation, the user of the present invention first connects the proximal end 60 of first tube segment 54 to fluid source 46 so that fluid flows by the force of gravity through lumen 39 and forces air downstream until the fluid reaches the point were valve device 16 is disposed within valve tube portion 18. With tube assembly 12 in its free state and disengaged from pump 14, valve device 16 is in the closed position and prevents fluid free flow through third tube segment 58. In the closed position illustrated in FIG. 3, second tube segment 56 is in a relaxed condition such that sealing member 28 of valve body 20 is securely seated against valve seat 25 of valve tube portion 18 in fluid tight engagement thereto. The user may then prime tube assembly 12 in order to evacuate remaining air from the tube assembly 12 by manually applying a tensile force along a portion of second tube segment 56 proximate valve tube portion 18. As shown in FIG. 4, applying a tensile force causes valve tube portion 18 to stretch such that valve body 20 is carried in the proximal direction relative to coupling 44 due to the flange 34 of valve body 20 being engaged and retained within groove 23. The act of stretching valve tube portion 18 causes sealing member 28 of valve body 20 to unseat from valve seat 25 and allow fluid free flow through valve device 16 which evacuates the remaining air from tube assembly 12.

To regulate and urge fluid flow after priming, tube assembly 12 is engaged to pump 14. Specifically, abutment surface 42 of drip chamber 40 is first positioned within first recess 50 by the user and second tube segment 56 is engaged around a portion of rotor 48. External flange 45 of tube assembly 12 is then inserted into second recess 52 such that a tensile force is applied along second tube segment 56 and places valve device 16 in the open position shown in FIG. 4. As the tensile force is applied along second tube segment 56, tube segment 56 becomes stretched and taut which carries valve device 16 away relative to coupling 44 and unseats sealing member 28 from valve seat 25, thereby permitting fluid flow through and around valve body 20 and into third tube segment 58. However, if tube assembly 12 becomes disengaged from pump 14 the tensile force applied along second tube segment 56 is released. Once the tensile force is released, valve device 16 is returned to the closed position shown in FIG. 3 as plunger portion 28 is driven back into fluid tight engagement against valve seat 25 and fluid free flow is prevented through tube assembly 12.

Figure 8:
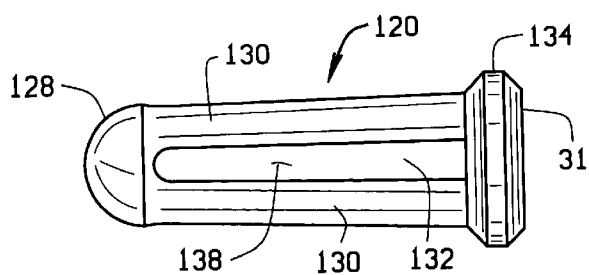
FIG. 8 is a side view of an alternative embodiment of the valve body according to the present invention.
Figure 9:
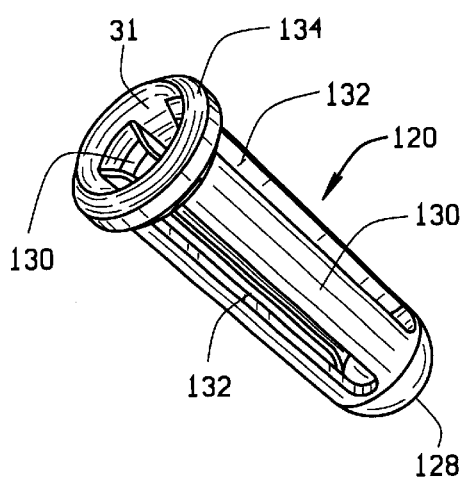
FIG. 9 is a perspective view of the alternative embodiment of the valve body according to the present invention.
Figure 10:
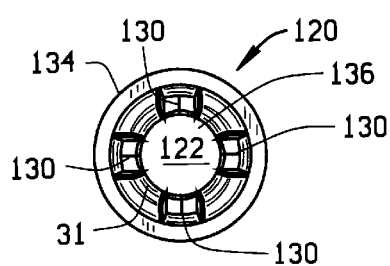
FIG. 10 is an end view of the alternative embodiment of the valve body according to the present invention.

Referring to FIGS. 8–10, an alternate embodiment of valve body 20 is shown. Valve body 120 is generally similar to the preferred embodiment in that body 120 comprises a sealing member 128 having a similar shaped dome configuration adapted to seat against valve seat 25 of valve tube portion 18. However, unlike the preferred embodiment, legs 130 of the alternative embodiment extend in a substantially straight fashion from sealing member 128 rather than being tapered as in the preferred embodiment. As shown specifically in FIG. 9, legs 130 terminate along the inner surface of an annular-shaped retention member 134 formed at the proximal end 31 of valve body 120 with a plurality of apertures 132 formed between each respective leg 130. As further illustrated in FIG. 10, flange 134 defines a generally circular opening 136 which communicates with apertures 132 through an inner chamber 138 defined between legs 130 that collectively define a fluid pathway through valve body 20 when valve device 120 is placed in the open position.

Figure 11:
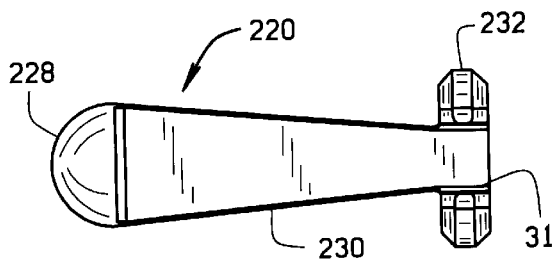
FIG. 11 is a side view of another alternative embodiment of the valve body according to the present invention.
Figure 12:
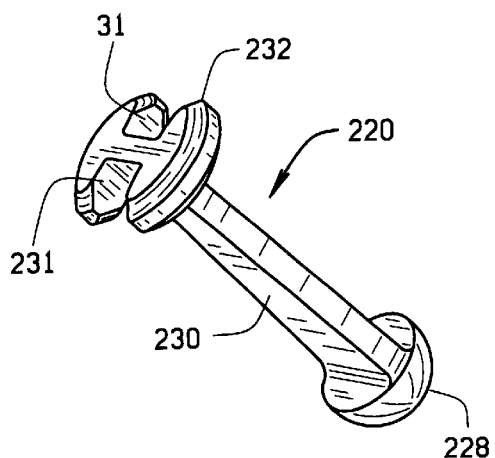
FIG. 12 is a perspective view of the alternative embodiment of the valve body shown in FIG. 11 according to the present invention.
Figure 13:
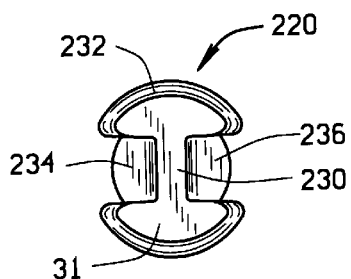
FIG. 13 is an end view of the alternative embodiment of the valve body shown in FIG. 11 according to the present invention.

Referring to FIGS. 11–13, another alternative embodiment of valve body 20 is shown. Valve body 220 of the alternative embodiment comprises a sealing member 228 having a similar shaped dome configuration as the other two embodiments. However, valve body 220 includes an elongated tapered shaft 230 which extends from sealing member 228 and terminates at retention member 232 formed at the proximal end 31 thereof. Retention member 232 of the alternative embodiment has a generally circular-shaped configuration adapted for retention inside groove 23 of valve tube portion 18 with opposing first and second channels 234, 236 defined on either side of member 230. As further shown, first and second channels 234, 236 provide fluid pathways through valve body 220 when valve device 16 is placed in the open position.

It should be understood from the foregoing that, while particular embodiments of the invention have been illustrated and described, various modifications can be made thereto without departing from the spirit and scope of the present invention. Therefore, it is not intended that the invention be limited by the specification; instead, the scope of the present invention is intended to be limited only by the appended claims.

We claim:

1. An anti-free flow device for preventing fluid free flow through a lumen of a tube assembly comprising:

a tube portion, said tube portion formed along the tube assembly and defining a channel and a valve seat formed across said channel, a body disposed inside said channel, said body including a sealing member with a plurality of legs extending therefrom, said sealing member being sealingly engageable against said valve seat, said body defining an inner chamber between said plurality of legs, said body further including at least one aperture formed between each set of said plurality of legs, said at least one aperture in communication with said inner chamber, said plurality of legs terminating at a retention member defining an opening, said retention member retaining said body inside said channel, said opening being in communication with said inner chamber for establishing a fluid pathway through said body.

2. The anti-free flow device according to claim 1, wherein said sealing member is disengaged from said valve seat when a tensile force is applied adjacent said tube portion.

3. The anti-free flow device according to claim 1, wherein said sealing member blocks fluid flow through said channel when said tube portion is in a relaxed condition.

4. The anti-free flow device according to claim 1, wherein said sealing member permits fluid flow through said channel when said tube portion is in a stretched condition.

5. The anti-free flow device according to claim 4, wherein when said tube portion is in a stretched condition fluid flow is permitted between said channel and said sealing member.

6. The anti-free flow device according to claim 1, wherein said sealing member has a dome-shaped configuration adapted for sealingly engaging said valve seat and preventing fluid free flow through said channel.

7. The anti-free flow device according to claim 1, wherein said at least one aperture is formed between said sealing member and said retention member.

8. The anti-free flow device according to claim 1, wherein said retention member includes at least one opening.

9. The anti-free flow device according to claim 1, wherein said channel includes a proximal section and a distal section, said proximal section of said channel has a groove.

10. The anti-free flow device according to claim 9, wherein said retention member is securely engageable within said groove.

11. The anti-free flow device according to claim 1, wherein said valve seat forms an opening.

12. The anti-free flow device according to claim 11, wherein said sealing member is engageable with said valve seat in a fluid tight seal whenever said tube portion is in a relaxed condition, thereby blocking fluid flow through said valve seat.

13. The anti-free flow device according to claim 12, wherein said sealing member disengages from said valve seat whenever said tube portion is in a stretched condition, thereby permitting fluid flow through said valve seat.

14. The anti-free flow device according to claim 1, wherein said tube portion is connected between the tube assembly and a connector of a fluid administration set.

15. An anti-free flow device for preventing fluid free flow in a tube administration set comprising:
   a flexible tube portion, said tube portion defining a channel and a valve seat formed across said channel, said channel further including a groove formed around the circumference of said channel;
   a body disposed in said channel, said body including a sealing member with a plurality of legs extending therefrom, said body defining an inner chamber between said plurality of legs, said sealing member being sealingly engageable against said valve seat, said body further including at least one aperture, juxtapositioned between each set of said plurality of legs said at least one aperture in communication with said inner chamber; and
   a retention member formed adjacent said body, said retention member defining an opening in communication with said inner chamber and said at least one aperature for establishing a fluid pathway through said body when a tensile force is applied to said flexible tube portion.

16. An anti-free flow device for preventing fluid free flow through a tube assembly comprising:
   a tube portion, said tube portion defining a channel and a valve seat formed across said channel,
   a body disposed inside said channel, said body including a sealing member with a plurality of legs extending therefrom, said sealing member being sealingly engageable against said valve seat, said body defining an inner chamber between said plurality of legs, said body further including at least one aperture formed between each set of said plurality of legs, said at least one aperture in communications with said inner chamber, and
   a retention member formed adjacent said body, said retention member defining an opening in communication with said inner chamber for establishing a fluid pathway through said body, said retention member being engageable with said groove for retaining said body inside said channel, wherein when said anti-free flow device is in a closed position said body is sealingly engaged against said valve seat, and when said anti-free flow device is in an open position, said body is disengaged from said valve seat.

17. The anti-free flow device according to claim 16, wherein said channel includes opposing distal and proximal sections, said distal section forming said valve seat and said proximal section forming a groove.

18. The anti-free flow device according to claim 16, wherein the anti-free flow device is placed in the open position when a tensile force is applied along the tube assembly adjacent said tube portion, thereby permitting fluid flow therethrough.

19. The anti-free flow device according to claim 17, wherein said retention member is engaged to said groove.

20. The anti-free flow device according to claim 18, wherein when the anti-free flow device is in the closed position said tensile force is released along said tube assembly, thereby preventing fluid flow through said tube assembly.

21. The anti-free flow device according to claim 16, wherein when the anti-free flow device is in the open position fluid flow is established through said fluid pathway.

22. An anti-free flow device connected to a tube assembly 12 comprising:
   a tube portion said tube portion including a channel and a valve seat interposed across said channel; and
   a body disposed within said channel, said body having a sealing member, an elongated shaft extending from said sealing member and terminating at a retention member having at least one channel formed therethrough,
   wherein said body blocks fluid free flow within said channel when said tube portion is in a relaxed condition and said body establishes fluid free flow when said tube portion is in a stretched condition.

23. The anti-free flow device according to claim 22, wherein said channel has a opposing proximal and distal sections, said proximal section forming a groove and said distal section defines said valve seat.

24. The anti-free flow device according to claim 23, wherein said retention member is securely retained within said groove when said tube portion is in a relaxed condition.

25. The anti-free flow device according to claim 23, wherein said sealing member is engaged in a fluid tight seal against said valve seat when said tube portion is in a relaxed condition.

26. The anti-free flow device according to claim 23, wherein said sealing member is disengaged from said valve seat when said tube portion is in a stretched condition.

27. The anti-free flow device according to claim 22, wherein a tensile force is applied to said tube portion when said tube portion is placed in a stretched condition.

* * * * *